(12) United States Patent
Biegun

(10) Patent No.: US 11,160,565 B2
(45) Date of Patent: Nov. 2, 2021

(54) RASP HOLDER FITTED WITH A HANDLE

(71) Applicant: XNOV IP, Luxembourg (LU)

(72) Inventor: Jean-Francois Biegun, Prrentruy (CH)

(73) Assignee: XNOV IP, Luxembourg (LU)

(*) Notice: Subject to any disclaimer, the term of this patent is extended or adjusted under 35 U.S.C. 154(b) by 293 days.

(21) Appl. No.: 16/261,814

(22) Filed: Jan. 30, 2019

(65) Prior Publication Data

US 2019/0159788 A1     May 30, 2019

Related U.S. Application Data

(63) Continuation of application No. 14/309,243, filed on Jun. 19, 2014, now abandoned.

(30) Foreign Application Priority Data

Jun. 26, 2013    (FR) ...................................... 13 01495

(51) Int. Cl.
     *A61B 17/16*         (2006.01)

(52) U.S. Cl.
     CPC ...... *A61B 17/1659* (2013.01); *A61B 17/1622* (2013.01); *A61B 17/1631* (2013.01); *A61B 17/1633* (2013.01); *A61B 17/1666* (2013.01)

(58) Field of Classification Search
     CPC ............ A61B 17/1622; A61B 17/1631; A61B 17/1633; A61B 17/1659; A61B 17/1666
     See application file for complete search history.

(56) References Cited

U.S. PATENT DOCUMENTS

| 6,053,922 A | * | 4/2000 | Krause | A61B 17/164 |
| | | | | 464/78 |
| 9,078,672 B1 | * | 7/2015 | Rosse | A61B 17/1671 |
| 2005/0038443 A1 | * | 2/2005 | Hedley | A61B 17/1666 |
| | | | | 606/91 |
| 2006/0217728 A1 | * | 9/2006 | Chervitz | A61B 17/1757 |
| | | | | 606/79 |
| 2007/0073302 A1 | * | 3/2007 | Myers | B25G 3/28 |
| | | | | 606/80 |

(Continued)

OTHER PUBLICATIONS

French Search Report dated Mar. 10, 2014 in related application No. FR 1301495.

(Continued)

*Primary Examiner* — Samuel S Hanna
(74) *Attorney, Agent, or Firm* — Renner Kenner Greive Bobak Taylor and Weber

(57) ABSTRACT

Tool holder, in particular a milling cutter holder, which comprises a main body with a substantially oblong cylindrical shape defining a channel in which a transmission passes designed to transmit to the tool, in particular the milling cutter, a movement from the axis of a drive motor, and a gripping element for gripping the tool holder, characterized in that an intermediate part is provided arranged between the transmission and the axis of the drive motor, the intermediate part comprising means for enabling the rotatable connection of said intermediate part to the transmission and the axis of the motor, the intermediate part comprising means forming an abutment designed to lock in translation in the longitudinal direction of displacement of the axis of transmission by abutment in particular against the gripping element.

13 Claims, 4 Drawing Sheets

(56) References Cited

U.S. PATENT DOCUMENTS

2007/0293869 A1    12/2007    Conte et al. .................... 606/91

OTHER PUBLICATIONS

Office Action dated Jul. 31, 2017 and response electronically filed thereto on Oct. 31, 2017 in related U.S. Appl. No. 14/309,243.
Office Action dated Dec. 27, 2017 and Responses electronically filed thereto on Apr. 13, 2018 and Aug. 1, 2018 in related U.S. Appl. No. 14/309,243.
Office Action dated Oct. 16, 2018 in related U.S. Appl. No. 14/309,243.

* cited by examiner

RASP HOLDER FITTED WITH A HANDLE

CROSS-REFERENCE TO RELATED APPLICATION

This application is a continuation of U.S. patent application Ser. No. 14/309,243 filed on Jun. 19, 2014, which claim priority from French Patent Application No. FR 13/01495 filed on Jun. 26, 2013, which are incorporated herein by reference in their entirety.

TECHNICAL FIELD

The present invention relates to a device forming a tool holder for cutting, rasping or removing bone, in particular a rasp holder or a milling cutter holder, in particular for rasping bone from a hip.

BACKGROUND ART

The tool holder, in particular the milling cutter holder, forms the interface between the tool, in particular the milling cutter, and a drive motor, in particular an electric motor, designed to drive the tool in rotation, in particular the milling cutter, in order to rasp the bone.

Milling cutter holders of this kind are already known. They are formed by a hollow body with an oblong, substantially cylindrical shape, defining an internal channel through which a transmission rod passes designed to provide transmission between on the one hand the milling cutter arranged at a distal end of the milling cutter holder and on the other hand an axis of rotation of the motor at a proximal end opposite the distal end. The device also comprises an element forming a handle for the surgeon to grip the tool holder.

Said milling cutter holders of the prior art need to be particularly robust to withstand the forces associated with the rotation of the motor and the action of the milling cutter during the rasping. As a result not only do these devices have a complex structure but they also wear out quickly.

DISCLOSURE OF THE INVENTION

The aim of the present invention is to overcome the disadvantages of the prior art by proposing a tool holder, in particular a milling cutter holder, which on the one hand has a simple structure, in particular simpler than those of the milling cutter holders of the prior art, and which on the other hand has greater longevity, being more resistant to the stresses and forces associated with the action of the rasp and the drive of the motor.

According to the invention, a tool holder, in particular a milling cutter holder is as defined in claim 1, refinements and preferred embodiments being defined in the subclaims 2 to 11.

By providing a body in two parts and in particular an auxiliary part supporting the gripping element, on the one hand the use of the tool holder is made easier and on the other hand its overall resistance to stresses associated with the action of the rasp and the drive of the motor is improved, the assembly being less rigid and the forces being better absorbed. Furthermore, it is easier to achieve locking in translation in the longitudinal direction of displacement of the axis of transmission of the transmission-motor axis interface, such that the transmission remains immobile in longitudinal direction and thus longitudinal displacements are avoided which are the cause of increased stress on the rest of the device, and in particular on the main body, which until now resulted in the premature wearing of the tool holder. Furthermore, as the main part of the body is subject to less stress the tool holder can have a simpler structure. In particular, if desired it is possible to do without elements in the main part of the body which are designed to dampen the effects associated with the displacement in translation (which no longer exists or which is much reduced in any case) of the transmission within the main part of the body. This results in a tool holder with a simpler structure, that is lighter and has greater longevity.

According to one refinement which itself also forms an independent embodiment of the invention described above but which can be used in combination with the latter in an advantageous manner, the transmission comprises at least two rods connected by a cardan joint formed by a fork coming from the rod, two half-forks coming from the rod and a half-pin and a single-piece brace.

BRIEF DESCRIPTION OF THE DRAWINGS

By way of example an embodiment of the invention will now be described in the following with reference to the drawings in which.

PREFERRED EMBODIMENT FOR CARRYING OUT THE INVENTION

Figure 1:
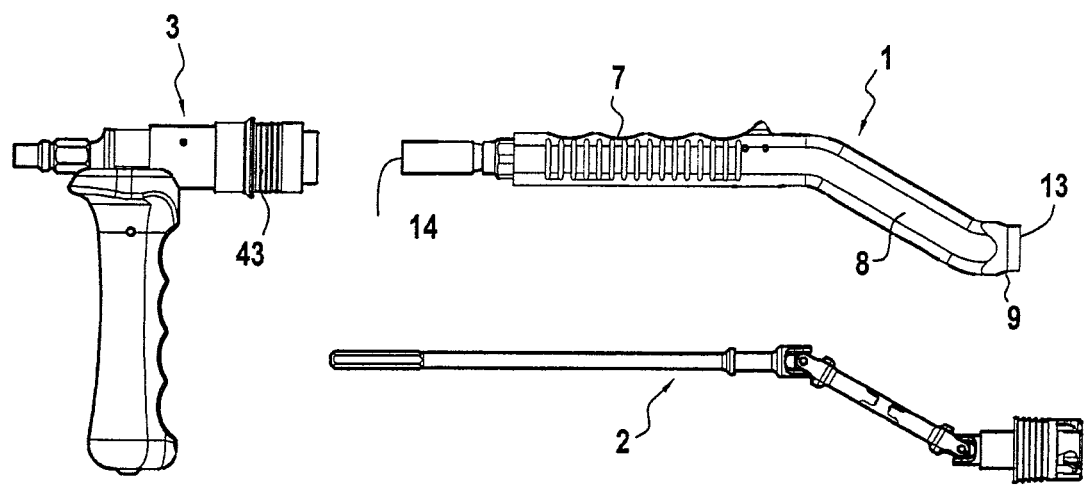
FIG. 1 is a view from the side of three main constituent elements of a tool holder device according to the invention.

FIG. 1 shows three main parts of a rasp holder according to the invention, a main part 1 of the body, a transmission element 2 and an auxiliary part 3 supporting a gripping element 22 respectively. The two parts 1 and 3, the main part and auxiliary part, distal and proximal part respectively, form in a general manner the body of the device which receives the transmission 2.

The main part 1 is an oblong element with a substantially cylindrical shape with a substantially square cross section and formed by a wall 4 from above and two lateral walls, the three walls, the top one and lateral walls, defining between them an internal channel 5 to the bottom and being designed to receive the transmission 2. The main part 1 also comprises a lateral distal opening 13 and a distal opening 14.

At its proximal end, the main part is terminated by a proximal section 6 with a substantially circular cross section with a smaller dimension than the rest of the main body. The channel 5 continues on the inside of the section 6 up to the proximal lateral opening 13, then into the auxiliary part 3 up to a proximal opening of the latter, delimited by a proximal edge 26.

Furthermore, the main part 1 is formed by three sections 7, 8, 9, two sections 7, 9 being parallel to one another whereas the intermediate section 8 is inclined relative to the two end sections 7 and 9, proximal and distal end sections, in particular by an angle of about 45°. This inclination, which is standard in the field of milling cutter holders, makes it possible to offset the axis of the milling cutter from the area obstructed by the soft tissue of the leg of the person in which the rasping is being performed, which simplifies the action of the surgeon. However, the present invention is not limited to this inclined form and it is also possible to provide, without departing from the scope of the present invention, a main body which has a straight cylindrical shape or has an inclined form with a different angle of inclination.

The transmission element 2 comprises four parts 10, 11, 12, 20 articulated in succession relative to one another, namely three parts 10, 11, 12 in the form of rods articulated by cardan systems and one connecting part 20 designed to provide the connection to the milling cutter.

The connecting part 20 comprises an element in the form of a tube threaded on the outside and is well known in the field so that it is not described in more detail above.

The proximal rod 10 comprises a distal section 15 the cross section of which has six sides, whereas the rest of the rod has a circular cross section.

The three articulated rods of the transmission 2, when in use extend into the channel 5, whilst the part 12 for connecting to the milling cutter projects out of the body through the distal opening 14. The proximal end of the rod 10 projects from the proximal lateral opening 13 of the body 1.

Figure 4:
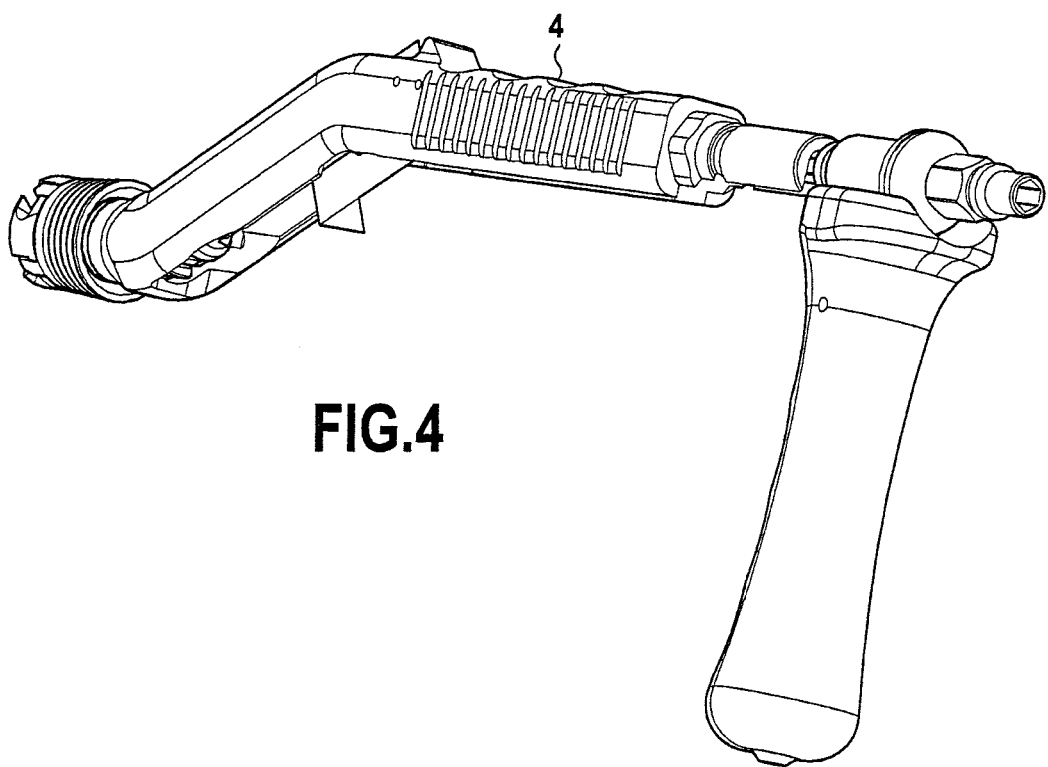
FIG. 4 is a perspective view of the tool holder of FIG. 1 in the assembled state but with the tube 21 and a connecting element between the auxiliary part supporting the gripping element and the main part of the body which have been omitted (these elements are represented in FIG. 1 however)
Figure 5:
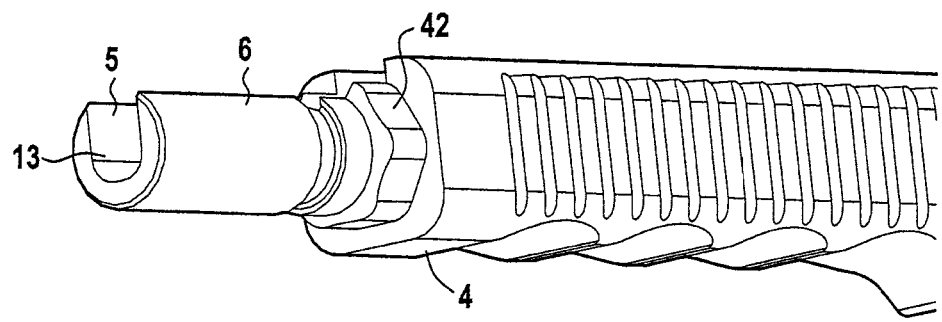
FIG. 5 is a perspective view of the part of the proximal end of the main part of the body of the tool holder of the preceding figures.

The auxiliary part 3 supporting the gripping element is formed by an element 21 in the form of a tube designed to receive at least a portion of the section 15 of the proximal end of the rod 10. Around the tube 21, a connecting ring 23 is mounted (shown in FIGS. 1 and 2, but not in FIG. 4) designed to ensure the connection between the auxiliary part 3 and the main part 1 of the body of the tool holder. A bar projects laterally from the proximal end of the tube 21. Said bar of any shape, but preferably elongated and with a circular cylindrical form in particular, is not shown in the figures as it is covered by an overmoulding 22 with a form adapted to the shape of the hand to enable the gripping of the tool holder.

The tube 21 of part 3 receives an element 23 made of an elastomer material comprising an element in the form of a tube 24 and a ring 25 projecting laterally from the tube 24 to form a shoulder designed to abut against the edge 26 of the proximal opening of the tube 21. Said elastomer element 23 absorbs the shocks and vibrations associated with the connection between the electric motor and the transmission 2, which connection is performed inside the tube 21 by means of an intermediate part 30 between the axis of the motor (not shown) and the section 15 of the proximal rod 10 of the transmission 2.

The intermediate part 30 comprises on the one hand a section 31 in the form of a tube designed to be inserted into the element 21 with the interposition of the elastomer tube 24. The distal section 21 in the form of a tube defines within it a passage for the transmission. Its cross section has a shape that is complementary to that of section 15 (in the embodiment shown here, the shape is 6 sided, but other shapes are also possible) to ensure the rotatable connection of the rod 10 of the transmission and the intermediate part 30.

A ring 32 projects laterally from the intermediate part 30 and is designed to abut against the edge 26 with the interposition of the elastomer ring 25 to thus prevent movement in the longitudinal direction of the transmission. The part 30 is terminated on the proximal side by a section 33 with a substantially cylindrical shape designed to connect with the axis of the motor (not shown). In particular, the section 33 comprises a blind bore 34 for receiving the axis of the motor having a cross section in the form of six sides.

The dimensions of tube 23 and tube 31 are such that the latter adapts to the force in the former, which itself adapts to the force in the tube 21 by passing through the opening 19 to thus ensure the fixing of the intermediate part 30 to the element 21 in the form of a tube of the gripping part.

Figure 2:
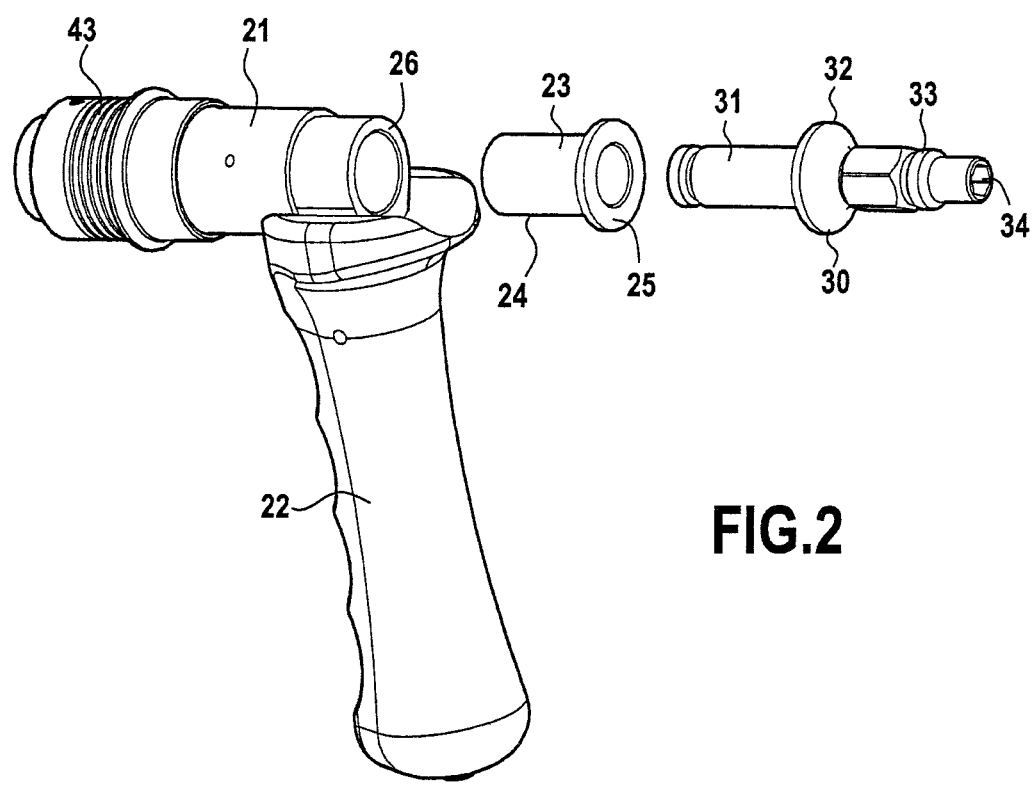
FIG. 2 is an exploded view in perspective of the auxiliary part comprising the gripping element of the device of FIG. 1, the intermediate connecting part between the transmission and the axis of the motor and the damping element being shown in the state removed from the auxiliary part, whereas in FIG. 1 they are shown in the inserted state.
Figure 6:
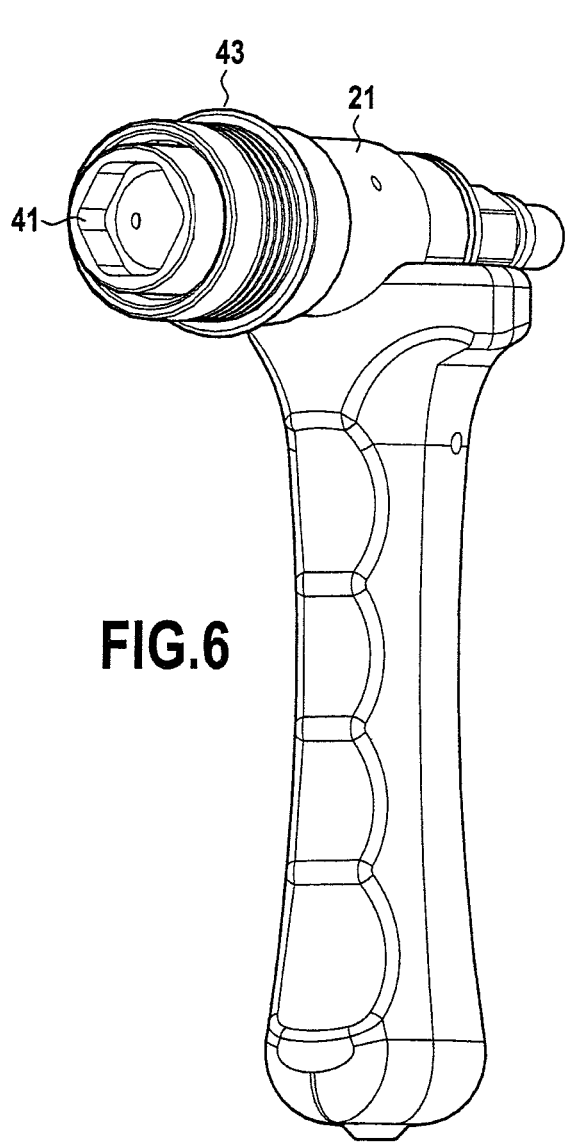
FIG. 6 is a perspective view of the distal side of the auxiliary part supporting the gripping element of FIGS. 1 to 4.
Figure 7:
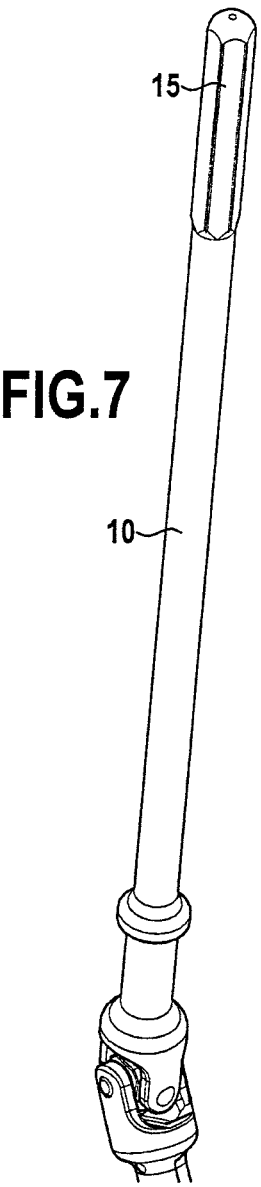
FIG. 7 is a more detailed perspective view of the proximal part of the transmission of the tool holder of the preceding figures.

FIG. 6 shows the other end that is not shown in FIG. 2. The element 21 in the form of a tube is extended by a tubular element 40, the distal opening 41 of which has a complementary shape to section 42 with 6 sides formed on the main body, followed distally by a section 6 of smaller diameter.

Figure 3:
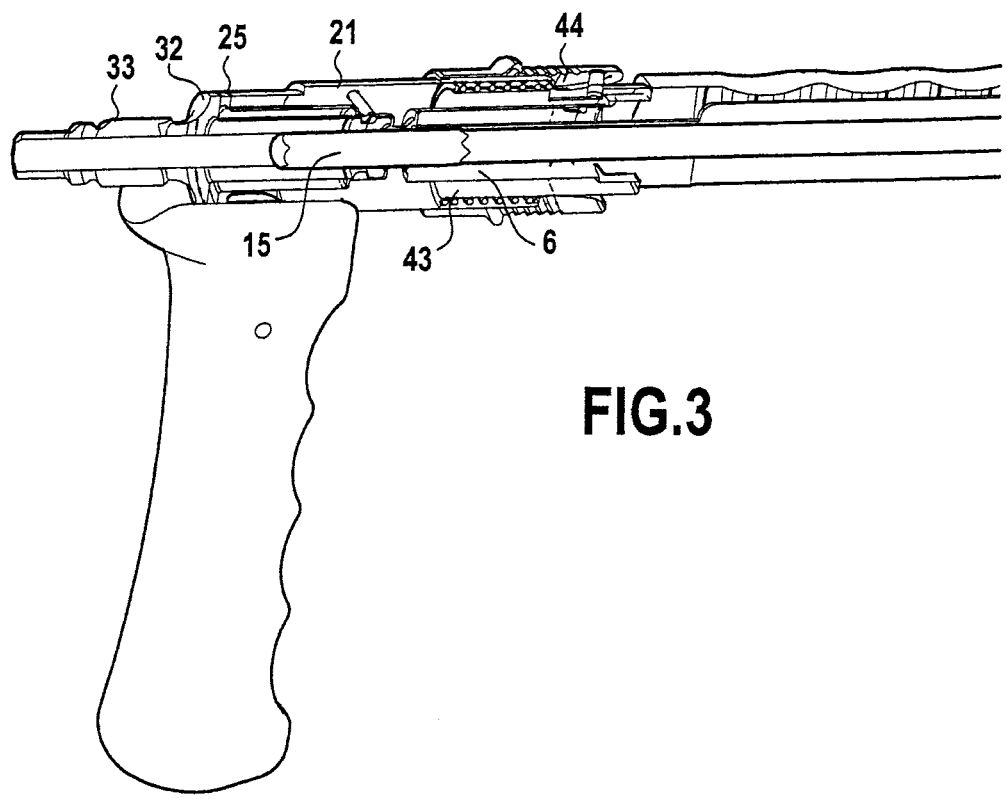
FIG. 3 is a longitudinal cross section of a part of the tool holder of FIG. 1, of the auxiliary part comprising the gripping element.

Thus the circular cylindrical section 6 penetrates, at the same time as the rod 10 of the transmission, into the tubular extension element 40 until the section 42 adapts to the opening 41 in order to lock in rotation the gripping element and the main body. The fixing of the two parts is then ensured by two rings 43 and 44 that are threaded and tapped respectively and joined respectively to the gripping element and the main body. The ring 43 is represented in the drawings in FIGS. 1, 2, 3 and 6 whereas the ring 44 is only shown in FIG. 3. When in use and in particular as shown in FIG. 3 in cross section, the tubes 24 and 31 are received in tube 21, the proximal end 15 of the rod 10 penetrating into the tube 31 of the intermediate part 30 by having a complementary form with the inner cross section of this element in the form of a tube 31, such that the element in the form of a tube is joined in rotation to the transmission 2. At the same time, the ring 32 presses against the ring 25 and against the proximal edge 26 of the opening of the tube 21 and the axis of the motor meshes with the blind bore 34, in order to join in rotation the axis of the motor with the transmission 2.

According to the invention, the motor, including the abutment 32 and the ring 25, is prevented from having an action in longitudinal direction relative to the axis of transmission 2, and consequently the axis of transmission 2 is much more stable in this longitudinal direction. As a result the transmission 2 remains more stable in the main body 1 and does not have the tendency to remove itself so that it is not necessary, as was the case in the prior art, to provide numerous locking bearings and/or securing devices for the various rods of the transmission in the body 1, 3. Furthermore, the body can be open on one side at least over one section, in particular along the main part 1 of the body, here towards the bottom, without this representing any problems, whereas in the prior art such an opening would be disadvantageous. As a result the structure of the body is lighter and simpler.

Furthermore, the cooperation of the opening 41 and the section 42 makes it possible for the surgeon to adjust from a plurality of possible orientations for section 42 relative to the gripping element, each orientation corresponding to a corresponding relative position of the form with 6 sides of the section in the opening having a cross section with 6 corresponding sides.

Figure 8:
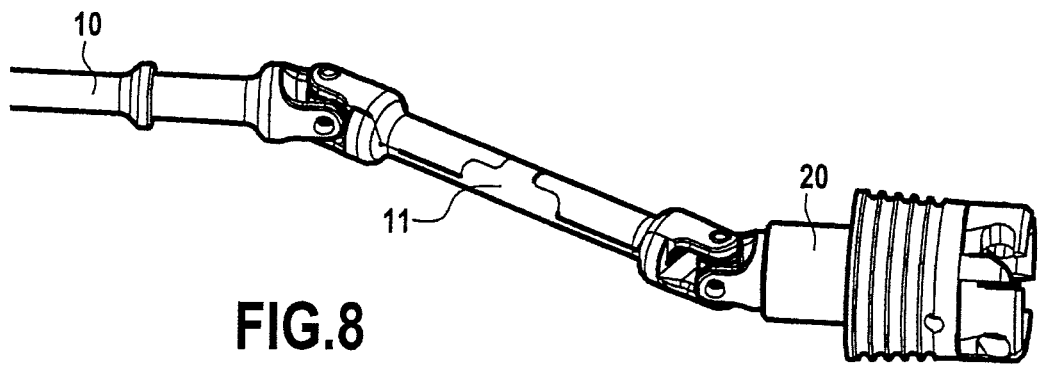
FIG. 8 is a perspective view of the distal part of the transmission of the tool holder assembly of FIG. 7.
Figure 9:
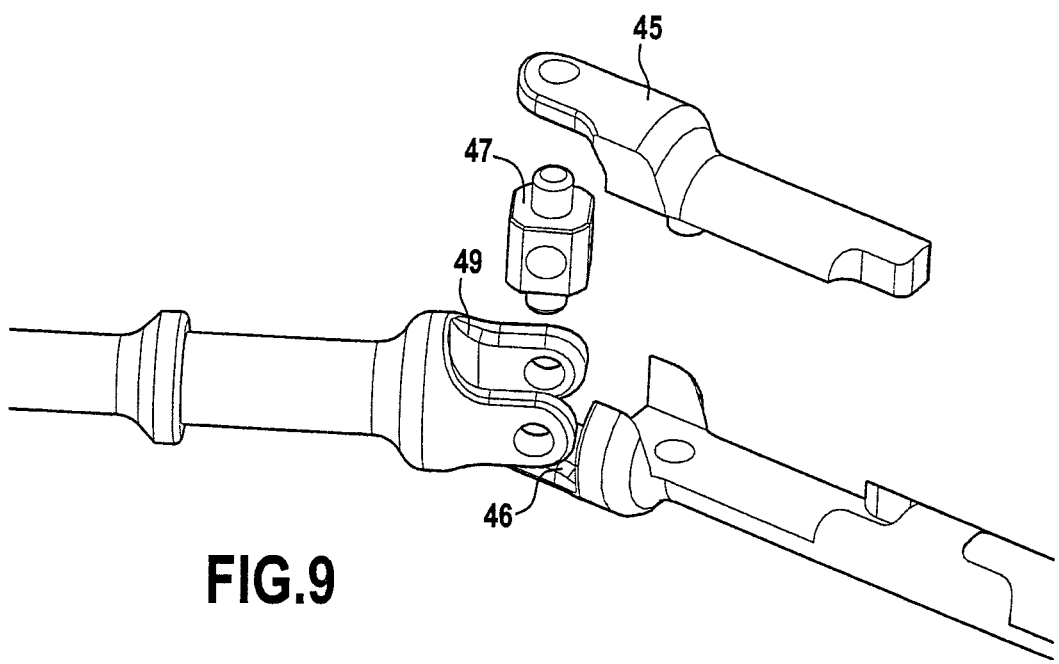
FIG. 9 is an exploded view on a larger scale of a part of FIG. 8.

FIGS. 8 and 9 show a particular embodiment of the transmission according to the invention which has an inventive aspect independent of the one described above.

FIG. 8 shows an exploded perspective view of the transmission 2. Between the two rods 10 and 11 the connection is a cardan joint. The latter is formed by a fork 44 coming from rod 10, two half-forks 45, 46 coming from rod 11 and a single-piece half-pin 47. The half-pin and the brace are single pieces. This considerably increases the mechanical resistance of the assembly and makes it possible to reduce the diameter of the joints. The frictional area of the pin/fork is more remote from the center of rotation, which reduces the stresses and the play and therefore the wear which enables the assembly of one of two forks formed in two shells. This assembly of two shells makes it possible to assemble the system which is no longer closed as in the prior art by half-pins, but by a whole pin.

Between the rod 11 and the connecting element 20, there is also a cardan joint, the fork coming from the rod 11 being also formed by two half forks that are identical to those at its other end.

By ensuring that the system for coupling to the motor and the system for adjusting the handle are coupled to the same bolt a device is obtained that is much simpler to use and/or a much more secure system is achieved. In fact, now when the handle needs to be adjusted it is sufficient to simply loosen the common bolt, which guarantees at the same time the disconnection of the motor, then once the handle has been adjusted the bolt is tightened ensuring both the locking of the handle in its correct position and the reconnection of the motor. It is thus ensured that the handle no longer needs to be adjusted while the motor is still in use. In this case it would also be necessary to disconnect the motor, which causes complications and may be dangerous.

What is claimed is:

1. A tool holder, in particular a milling cutter holder, comprising a transmission rod, a substantially oblong body defining a channel extending along a longitudinal direction and receiving said transmission rod which is designed to transmit to the tool a movement from an axis of a drive motor, wherein the body is formed of at least two distinct parts, namely a distal main part and a proximal auxiliary part, the channel having a respective section defined in each part of the distal main part and the proximal auxiliary part, and a gripping element for gripping the tool holder, the gripping element being fixed to the proximal auxiliary part of the body and a most proximal point of the transmission rod being located in the section of the channel defined by the proximal auxiliary part of the body, wherein an intermediate part being provided proximally to the transmission rod and being intended to come into contact with the axis of the drive motor, the intermediate part being removably joined in rotation with the transmission rod and being intended to be removably joined in rotation with the axis of the drive motor, wherein said intermediate part comprises an abutment means in the form of a ring which abuts against a proximal opening edge of said proximal auxiliary part, and wherein said gripping element projects laterally from said auxiliary proximal part at the level of said ring of said intermediate part.

2. The tool holder according to claim 1, characterized in that the two distinct parts, the distal main part and the proximal auxiliary part, are arranged consecutively.

3. The tool holder according to claim 2, characterized in that the two distinct parts, the distal main part and the proximal auxiliary part, are fixed to one another in a detachable manner by a detachable securing means.

4. The tool holder according to claim 3, characterized in that the detachable securing means comprises two rings joined respectively to the main distal part and the proximal auxiliary part.

5. The tool holder according to claim 1, characterized in that a means is provided for adjusting a relative orientation in rotation of the proximal auxiliary part to the distal main part by the cooperation of a section with six sides of the distal main part with an opening with a cross section of six sides of the proximal auxiliary part.

6. The tool holder according to claim 1, characterized in that the intermediate part is received partly in the proximal auxiliary part and is joined in rotation with the transmission rod.

7. The tool holder according to claim 1, characterized in that the proximal auxiliary part receives within it an elastomeric element made from an elastomer material comprising an element in the form of an elastomeric tube, and an elastomeric ring projecting laterally from said elastomeric tube to form a shoulder abutting against an edge of a proximal opening of the proximal auxiliary part.

8. The tool holder according to claim 7, characterized in that the intermediate part comprises a tube-shaped section inserted into said proximal auxiliary part with the interposition of the elastomeric tube element.

9. The tool holder according to claim 7, characterized in that said ring of said intermediate part projects laterally from the tube-shaped section and abuts against the proximal opening edge of the proximal auxiliary part with the interposition of the elastomeric ring to thus prevent movement in the longitudinal direction.

10. The tool holder according to claim 1, characterized in that the intermediate part is terminated at a proximal end by a section with a substantially cylindrical form designed for connection with the axis of the drive motor.

11. The tool holder according to claim 1, characterized in that the transmission rod comprises a first rod and a second rod connected by a cardan joint formed by a fork coming from said first rod, two half-forks coming from said second rod and a half-pin.

12. The tool holder according to claim 1, characterized in that the intermediate part further comprises a tube-shaped section inserted into said proximal auxiliary part.

13. The tool holder according to claim 12, characterized in that said ring of said intermediate part projects laterally from the tube-shaped section and abuts against the proximal opening edge of the proximal auxiliary part.

* * * * *